(12) United States Patent
Pedrotti et al.

(10) Patent No.: US 6,783,081 B2
(45) Date of Patent: Aug. 31, 2004

(54) MOBILE COMBUSTION EXHALER FOR THE VAPORIZATION OF INSECTICIDE OR PERFUMED SUBSTANCES HAVING A LOW VAPOR PRESSURE AND COMBUSTIBLE REFILL FOR SAID EXHALER

(75) Inventors: Andrea Pedrotti, Pietramurata (IT); Filippo Stenico, Trento (IT); Walter Sordo, Trento (IT)

(73) Assignee: Zobele Holding S.p.A., Trento (IT)

( * ) Notice: Subject to any disclaimer, the term of this patent is extended or adjusted under 35 U.S.C. 154(b) by 223 days.

(21) Appl. No.: 09/930,155

(22) Filed: Aug. 16, 2001

(65) Prior Publication Data
US 2002/0023968 A1 Feb. 28, 2002

(30) Foreign Application Priority Data
Aug. 17, 2000 (IT) .................................. MI2000A001892

(51) Int. Cl.⁷ ................................................ B05B 1/24
(52) U.S. Cl. ........................ 239/136; 239/135; 239/326; 422/125; 422/126; 43/127
(58) Field of Search ................................. 239/135, 136, 239/326; 392/386, 390, 392; 43/125, 127, 129, 132.1, 1; 422/124, 125, 126; 222/146.1, 146.2, 146.5

(56) References Cited

U.S. PATENT DOCUMENTS

| | | | | |
|---|---|---|---|---|
| 2,742,342 A | * | 4/1956 | Dew et al. | ...................... 422/37 |
| 4,771,563 A | * | 9/1988 | Easley | ......................... 239/136 |
| 4,839,144 A | * | 6/1989 | Martin | ........................ 422/126 |
| 4,959,925 A | * | 10/1990 | Nelson et al. | ................. 43/127 |
| 5,094,025 A | * | 3/1992 | Daniels | ....................... 239/136 |
| 5,161,646 A | * | 11/1992 | Aurich et al. | ............. 222/146.5 |
| 5,555,665 A | * | 9/1996 | Fore | ............................ 43/129 |
| 6,061,950 A | * | 5/2000 | Carey et al. | ................... 43/127 |
| 6,286,248 B1 | * | 9/2001 | Bryant et al. | ................. 43/125 |

* cited by examiner

Primary Examiner—Steven J. Ganey
(74) Attorney, Agent, or Firm—Young & Thompson

(57) ABSTRACT

A combustion exhaler for the vaporization of an insecticide or perfumed substance, comprises a housing (1, 2) having intake and exit vents (4), and a solid porous combustible element (6, 9) impregnated with said substance, placed inside said housing between said intake and exit vents, and fixed onto appropriate support means. The combustible element shows a high ratio between the mass of the active substance and the mass of the combustible element and, in one embodiment, a low mass/length ratio.

24 Claims, 2 Drawing Sheets

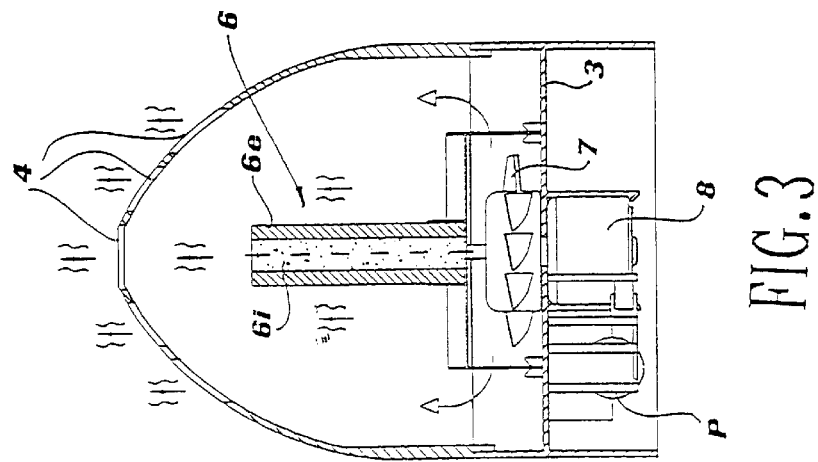
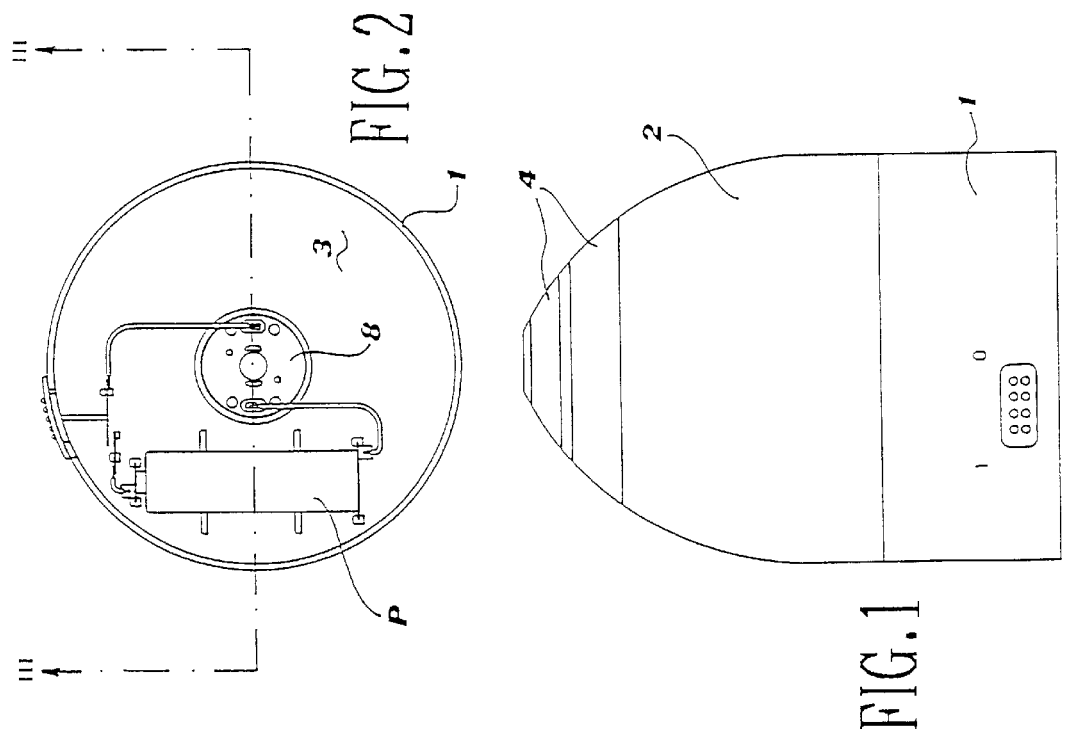

MOBILE COMBUSTION EXHALER FOR THE VAPORIZATION OF INSECTICIDE OR PERFUMED SUBSTANCES HAVING A LOW VAPOR PRESSURE AND COMBUSTIBLE REFILL FOR SAID EXHALER

BACKGROUND OF THE INVENTION

The present invention refers to a mobile combustion exhaler for the vaporization of insecticide or perfumed substances having a low vapor pressure, and in particular to an exhaler of such a type which can be used both for an extended action of destruction of flying insects, such as mosquitoes, flies, gnats and similar, and for a fast disinfestation from creeping insects, such as ants, beetles, spiders, fleas and similar as well as a perfume dispenser for environments.

The present invention also refers to the refills which can be used with said exhaler.

Different types of exhalers are spread on the market, which types can be gathered into the two big categories of electric and combustion exhalers, hereunder shortly described.

The electric exhalers generally consist of an electric heating device and of a support impregnated with the active substance to be vaporized, said support being placed nearby the heating device.

These devices are designed to be used in closed rooms and with active substances having a medium or high vapor pressure; the temperatures which can be obtained by these devices, in fact, are limited both by the mechanical strength of the plastic support parts and by fire fighting and accident prevention security: therefore said temperatures generally range between 60 and 200° C.

The combustion exhalers, instead, comprise a porous combustible support impregnated with an active substance to be evaporated in the environment during the gradual complete burning of the same support. Exhalers of such a type, are substantially made of the only combustible refill and of a support apt to maintain in an appropriate position the same refill during the combustion thereof.

Fumigators in coil-shape, for example, are largely spread on the market, but other kind of supports, such as short thick candles and similar devices, are also known. In all these cases, such exhalers are designed to be prevalently used in external environments, considering that during the combustion, a contemporary plenty production of smoke, due to the burning of the support, takes place. Considering the high temperature in the combustion area, said exhalers can be also used with active substances having a low vapor pressure, which substances are preferred since they do not show any loss of active substance during storage at ambient temperature.

The combustion exhalers have the considerable advantage, with regard to the electric exhalers, that can be also used in places where an electric outlet is not immediately available as, for example, in places far away from houses, inside rooms without electric current such as cellars and storages, in highland or other scarcely populated regions or, finally, in emerging countries wherein the electric network still has a low expansion and capillarity and wherein, however, the presence of insects not only is irritating, but can be even very dangerous as the insects are potential carriers of serious illness, such as for example malaria.

In these last situations, the use of combustion exhalers has largely widespread, but it is still limited by the intrinsic characteristics of the exhalers which are nowadays available on the market. In said exhalers in fact, the combustible support must be self-supporting from the mechanical point of view, as well as guarantee the maintenance of a good combustion even in presence of adverse climatic conditions (wind, humidity and similar); for making up for said requirements, the combustible support must therefore have a relatively high mass with regard to its own longitudinal dimension, as well as a low concentration of the liquid active substance. As a consequence of the above said features the mass of the combustible support burnt for unity of time is rather high and a high quantity of smoke is therefore produced during the combustion. The presence of high quantities of smokes obviously excludes the possibility of a safe use of the exhaler in closed rooms, particularly with a contemporary human presence, and therefore a large spreading of these products has been seriously limited, while, on the contrary it would be largely desirable for allowing an appropriate control of noxious insects in environments which do not dispose of electric current.

SUMMARY OF THE INVENTION

The object of the present invention is to thus supply a new type of combustible exhaler, free from the above complained drawbacks and apt to be used both in closed rooms and open environments for the vaporization of active substances, and in particular insecticide products, even having a low vapor pressure.

A further object of the present invention is to supply an exhaler of such a type which can be used, by simply replacing the type of refill, both for an extended action at slow combustion for destroying flying insects with the contemporary human presence, and for a quick action at fast combustion for destroying creeping insects, without human presence in the treated rooms.

Such a object has been achieved, according to the present invention, by means of a combustion exhaler for the vaporization of an insecticide or perfumed substance characterised in that it comprises a housing having intake and exit vents, a solid porous combustible element impregnated with said substance, placed into said housing, between said intake and exit vents, and fixed to the same through appropriate support means, said combustible element having an high ratio between the mass of the active substance and the mass of the combustible element.

According to a feature of the invention, said combustible element also shows a low mass/length ratio. In an embodiment of the invention, particularly suitable for an extended use in closed rooms with the human presence, said ratio is so reduced that said element does not have a mechanical self-supporting feature.

According to a further feature of the invention, said support means of the combustible element extend for the whole length of the same combustible element.

According to still another feature of the invention fan means are provided into said housing, apt to produce an air flow between said intake and exit vents of the housing.

BRIEF DESCRIPTION OF THE DRAWINGS

Further features and advantages of the present invention will anyhow result more evident from the following detailed description of preferred embodiments of the same, as illustrated in the enclosed drawings, wherein:

FIG. 1 shows a front view of the exhaler according to the present invention, incorporating a first embodiment of the refill, particularly apt to the fast disinfestation from creeping insects;

FIG. 2 is a bottom plan view of FIG. 1, showing the driving motor of a fan and the relative feeding battery;

FIG. 3 is a section view along the line III—III of FIG. 2;

DETAILED DESCRIPTION OF THE PREFERRED EMBODIMENTS

Figure 4:
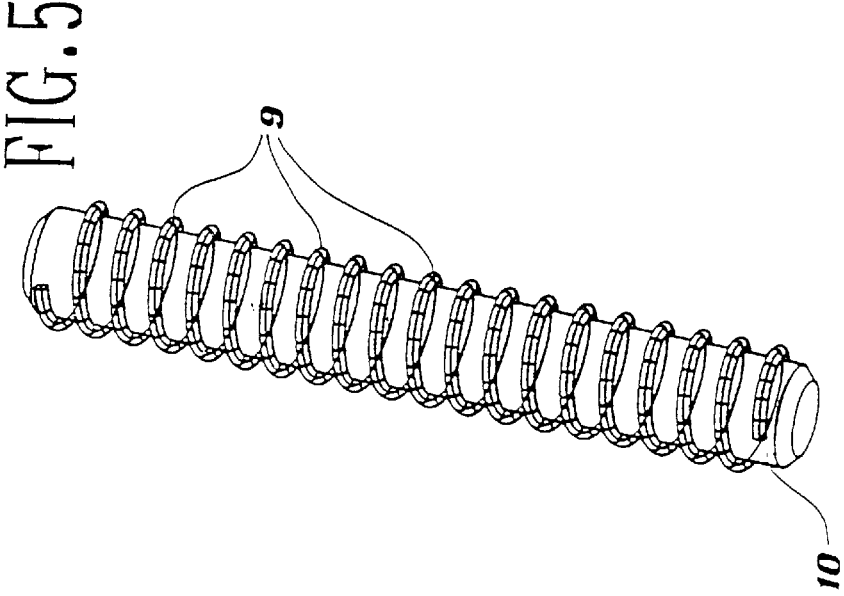
FIG. 4 is a perspective view of a second embodiment of the exhaler refill, particularly apt to the destruction for long period terms of flying insects.

Making reference to FIGS. 1 to 3, it can be seen how the structure of the exhaler according to the present invention is particularly simple and strong, and so suitable for a mobile use of the same exhaler, which can be therefore used in closed rooms as well as in open places, without electric current being available.

The exhaler comprises an external housing, formed by a base support 1 and a covering cap 2, apt to be snap-inserted into said base. The base 1 is open in the bottom part and separated from the upper area of the exhaler by a baffle 3 provided with one or more air intake vents. Corresponding exit vents 4 of the air flow are provided in the higher part of the cap 2.

In the central part of the baffle 3 a seat 5 for fixing a combustible refill 6 is provided, under of which, optionally, a little fan device 7 may be also provided. Said fan device 7 is controlled by an electric motor 8, positioned into the base 1 of the exhaler under the baffle 3. Considering the small power requested by the fan device 7, the motor 8 can be fed for a long working term, for example of a week, by a common battery P.

The particular structure of the exhaler according to the present invention—on the contrary of known products spread on the market, such the above mentioned fumigators in coil shape and the short thick candles—allows to have a more regular and protected combustion of the combustible element, also with adverse climatic conditions. According to an important feature of the present invention, the above said conditions allow to use combustible elements wherein the ratio of the active substance impregnated within the combustible element, is far higher than the one which used up to now in the known combustible exhalers, obtaining therefore, under the same efficacy conditions, a very reduced production of combustion smokes. In fact, while in the known products the ratio between the mass of the active substance (in mg) and the mass of the combustible element (in g) ranges from some tenth up to a maximum value of 5 mg/g, in the combustible element of the exhaler according to the present invention, said ratio is comprised in the range from 10 to 300 mg/g and, preferably, in the range from 100 to 200 mg/g.

FIG. 3 shows a first type of refill 6, particularly suitable for a quick disinfection of creeping insects. For this kind of use, the contents of active substance vaporized in the environment must be particularly high, and said quantity must be vaporized in a relatively short term. These two conditions in fact allow to obtain an high concentration of active substance into the ambient air and thus to flush and destroy even the insects which have found shelter in cracks of walls, behind furnitures and similar.

However said conditions are also reciprocally incompatible, since a quick combustion would request a combustible element having a small mass and a low concentration of active substance, which element would be thus absolutely unsuitable to contain the high quantity of liquid active substance which is necessary for this kind of treatments.

All the above said problems are solved by the refill 6 according to the first embodiment of the invention. This refill consists in a thin external layer 6e having the shape of an hollow cylinder made from a dry combustible material, and in an internal cylindrical core 6i made from a combustible material impregnated with an high concentration of active substance and therefore not directly combustible.

The exhaler is activated by lighting the external layer 6e of the same; the heat deriving by the combustion of said layer, causes the vaporization of the active substance contained in the core 6i and consequently its progressive drying, so that even the core 6i gradually burns out, completing the vaporization of the active substance contained therein.

In a first version of this embodiment, the internal core 6i of the refill 6, instead, is formed by a cylinder of porous incombustible material, such as, for example, a ceramic material impregnated with the active substance. In such a case, the vaporization of the active substance is fully provided by the heat developed from the combustion of the hollow dry cylinder 6e enveloping the core 6i.

In a second version of this embodiment, apt to be used for the disinfection of flying insects in a short-medium term—which version contains therefore a lower quantity of the active substance in respect of the previous mentioned cases—the combustible element formed by the hollow cylinder 6e is directly impregnated with all the active substance. The central core 6i in such a case consists of a solid not porous cylinder which exclusively serves as a support for the combustible element 6e and which can be also missing at all.

The combustible element impregnated with the active substance can be produced by preparing a cylinder made from a dry porous material, and subsequently impregnating in the same with the liquid active substance, or alternatively by extruding said cylinder from a mixture of combustible material and active substance.

Figure 5:
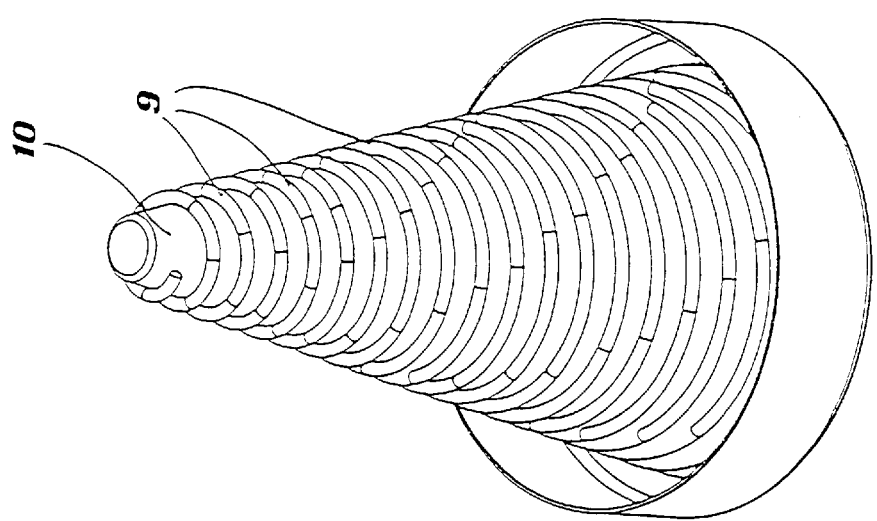
FIG. 5 is a perspective view of a version of the second embodiment of the exhaler refill.

FIGS. 4 and 5 show a second embodiment of the invention, particularly apt to be used in destroying flying insects in a long term. In this embodiment the combustible element is formed by an extended body 9, namely a body having the longitudinal dimension higher than the two transversal dimensions, such as, for example, a yarn, a plait, a string or similar. The above said combustible element, impregnated with the active substance, has moreover a very low ratio between its mass and length; a combustible element of such a type shows therefore, during its combustion, a very low smoke emission and it can therefore be also used in the extended disinfection of closed rooms with the human presence.

Considering the low mass/length ratio, said combustible element does not have however any self-supporting feature. For this reason, according to the invention, it is foreseen that said element be wound up as a spiral onto a not porous or incombustible solid support core 10, apt to be positioned inside the exhaler.

FIG. 4 shows a first version of this second embodiment, wherein the incombustible support 10 has a conical configuration. FIG. 5 shows a second version, wherein the incombustible support 10 has a cylindrical configuration.

From the previous description, it should be evident that the exhaler of the present invention has fully achieved the desired objects, providing a sure and reliable device for the insects disinfection both of the extended type, at low concentration of active substance, and of the fast type, at high concentration of the active substance. The device is practical, cheap, mobile and can be used without making use of electric current.

Where standard electric batteries are available, the device can be fitted out with a forced fan system so as to reduce the transient time in closed rooms or to broaden the action area of the device in open places.

The present invention has been described with regard to preferred embodiments thereof, but it must be clear that a skilled person in the field could conceive different versions thereof, without departing from the scope of the invention, as far as comprised in the following definitions given.

What is claimed is:

1. Combustion exhaler for the vaporization of insecticide or perfumed substances comprising:

a housing having intake and exit vents, and a solid porous combustible element impregnated with said substance, placed into said housing, between said intake and exit vents, and fixed to the same through appropriate support means, said combustible element having a high ratio between the mass of the active substance and the mass of the combustible element, wherein the ratio between the mass of the active substance and the mass of the combustible element, ranges between 10 and 300 mg/g.

2. Exhaler as in claim 1, wherein said combustible element consists of an extended body, having its longitudinal dimension much higher than its two other transversal dimensions and further having a low ratio between its mass and its longitudinal dimension.

3. Exhaler as in claim 2, wherein the ratio between the mass of said combustible element and its length, is such that said element does not show a mechanical self-supporting features.

4. Exhaler as in claim 2, wherein said support means of the combustible element extend for the whole length of the same combustible element.

5. Exhaler as in claim 2, wherein said combustible element, is formed by a string comprising one or more strands, which string is impregnated with said insecticide or perfumed substance and wound up as a spiral onto a solid incombustible core.

6. Exhaler as in claim 5, wherein said incombustible solid core has a conical shape.

7. Exhaler as in claim 5, wherein said incombustible solid core has a cylindrical shape.

8. Exhaler as in claim 1, wherein said combustible element is formed by a hollow cylinder having a small thickness, impregnated with said insecticide or perfumed substance.

9. Exhaler as in claim 8, wherein said cylinder is made by extruding a mixture of combustible material and insecticide or perfumed substance.

10. Exhaler as in claim 8, wherein said cylinder is made at a dry state and is subsequently impregnated with said insecticide or perfumed substance.

11. Exhaler as in claim 1, wherein said combustible element comprises a hollow dry cylinder having a small dry thickness, housing therein a porous cylinder impregnated with said insecticide or perfumed substance.

12. Exhaler as in claim 11, wherein said porous cylinder is made from a combustible material.

13. Exhaler as in claim 11, wherein said porous cylinder is made from an incombustible material.

14. Exhaler as in claim 1, wherein fan means apt to produce an air flow are provided within said housing and between said intake and exit vents, said fan means being driven by a motor fed through electric batteries.

15. Exhaler as claimed in claim 1, wherein the ratio between the mass of the active substance and the mass of the combustible element, ranges between 100 and 200 mg/g.

16. Combustible refill for an insecticide or perfumed exhaler, said combustible refill comprising a combustible element having a low mass/length ratio, such that said element does not show any mechanical self-supporting features, and a solid support of said element, wherein said combustible element is a hollow cylinder having small thickness, impregnated with said insecticide or perfumed substance.

17. Refill as in claim 16, wherein said cylinder is made by extruding a mixture of a combustible material and said insecticide or perfumed substance.

18. Refill as in claim 16, wherein said cylinder is made at a dry state and is subsequently impregnated with said insecticide or perfumed substance.

19. Combustible refill for an insecticide or perfumed exhaler, said combustible refill comprising a combustible element having a low mass/length ratio, such that said element does not show any mechanical self-supporting features, and a solid support of said element, wherein said combustible element comprises a hollow dry cylinder having a small thickness, housing therein a porous cylinder impregnated with said insecticide or perfumed substance.

20. Refill as in claim 19, wherein said porous cylinder is made from a combustible material.

21. Refill as in claim 19, wherein said porous cylinder is made from an incombustible material.

22. Combustible refill for an insecticide or perfumed exhaler, said combustible refill comprising a combustible element having a low mass/length ratio, such that said element does not show any mechanical self-supporting features, and a solid support of said element, wherein said combustible element is formed by a string comprising one or more strands, said string is impregnated with said insecticide or perfumed substance and wound up as a spiral onto a solid incombustible core.

23. Refill as in 22, wherein said solid incombustible core has a conical shape.

24. Refill as in 22, wherein said solid incombustible core has a cylindrical shape.

* * * * *